United States Patent [19]

Mercier et al.

[11] Patent Number: 5,102,581
[45] Date of Patent: Apr. 7, 1992

[54] PROCESS FOR THE PREPARATION OF PSEUDOIONONE USING OXIDATIVE DECARBOXYLATION

[75] Inventors: Claude Mercier, Lyon; Gérard Mignani, Livry-Gargan, both of France

[73] Assignee: Rhone-Poulenc Sante, Antony Cedex, France

[21] Appl. No.: 541,797

[22] Filed: Jun. 21, 1990

[30] Foreign Application Priority Data

Jun. 22, 1989 [FR] France ................................ 89 08317

[51] Int. Cl.$^5$ .............................................. C09F 7/02
[52] U.S. Cl. .................................. 554/115; 568/384; 568/413
[58] Field of Search ...................... 260/398, 405.6, 406; 568/384, 413

[56] References Cited

PUBLICATIONS

Tsuji, Peere & Applied Chemistry, vol. 58, #6, Dec. 1986, pp. 869-878.
Tsugi et al., J. Organic Chemistry, vol. 50, #18, 1985, pp. 3416-3417.
Shimizu et al., J. Am. Chem. Soc., vol. 104, #21, 1982, pp. 5844-5846.
Migrane et al., Tetra Hedson Letters, vol. 27, #23, 1986, pp. 2591-2594.
Mignani. Ichiro et al., Synthesis, Nov. 1987, pp. 992-995.

*Primary Examiner*—Jose G. Dees
*Assistant Examiner*—Deborah Carr
*Attorney, Agent, or Firm*—Finnegan, Henderson, Farabow, Garrett, and Dunner

[57] ABSTRACT

Process for the preparation of:

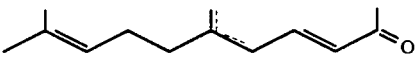

by oxidative decarboxylation of an allyl β-ketoester:

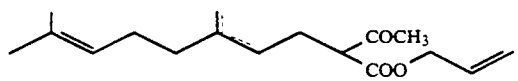

in an organic solvent, in the presence of a palladium-based catalyst. The organic solvent selected from an amide, a nitrile, or a dinitrile.

10 Claims, No Drawings

PROCESS FOR THE PREPARATION OF PSEUDOIONONE USING OXIDATIVE DECARBOXYLATION

BACKGROUND OF THE INVENTION

The present invention relates to a new process for the preparation of pseudoionone, which is an intermediate of particular interest in synthesizing vitamin A.

French Patent 2,518,538 discloses the preparation of pseudoionone by treating, in a basic polar aprotic solvent, a chlorinated β-ketoester of formulas Ia or Ib:

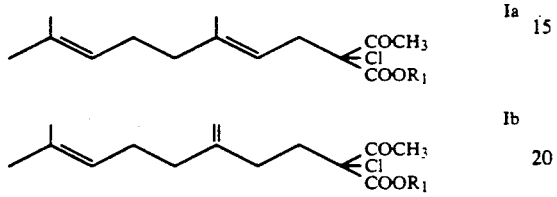

wherein $R_1$ represents an alkyl radical containing 1 to 4 carbon atoms, with a lithium chloride - inorganic acid - tertiary amine system at a temperature between 80° C. and 160° C. Formulas Ia and Ib can be obtained by reacting cupric chloride and a compound of formulas IIa and IIb:

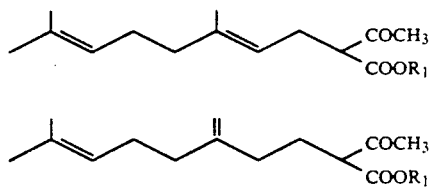

wherein $R_1$ has the same definition as $R_1$ above, in the presence of lithium chloride in a basic aprotic solvent. Compounds of Formulas of IIa and IIb are obtained by the reaction of an alkyl acetylacetate on myrcene under the conditions described in European Patent EP 44,771.

I. Minami et al., Synthesis, p. 992 (1987) and French Patent 2,526,420 teach that the oxidative decarboxylation can be performed only on α,α-disubstituted allyl β-ketoesters:

SUMMARY OF THE INVENTION

According to the present invention, pseudoionone of formulas IVa or IVb can be obtained by oxidative decarboxylation of α-monosubstituted allyl β-ketoesters of formulas IIIa or IIIb:

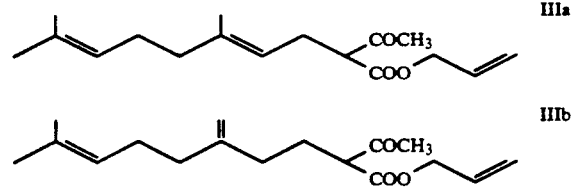

in an organic solvent selected from amides, such as dimethylformamide; nitriles, such as acetonitrile; and dinitriles, such as methylglutaronitrile, adiponitrile, and 1,6-dicyanohexane, in the presence of a palladium-based catalyst, such as palladium acetate Pd(OAc)$_2$ or bis(-dibenzylidene-acetone)palladium Pd(dba)$_2$. Optionally, the decarboxylation is carried out in the presence of a ligand such as a phosphine, for example triphenylphosphine or diphenylphosphinoethane. The decarboxylation is preferably carried out at a temperature between about 0° C. and the reflux temperature of the reaction mixture.

DETAILED DESCRIPTION OF THE INVENTION

The process according to the invention is performed by using either formula IIIa or formula IIIb separately or as a mixture. Depending on certain conditions, as described below, compounds of formulas IVa, IVb and IVc are produced separately or as a mixture:

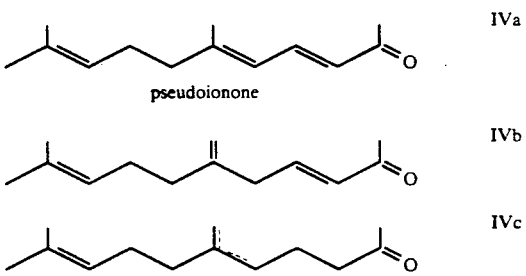

pseudoionone

Formula IVb is easily isomerized to pseudoionone of formula IVa according to the techniques described by Y. Fujita et al., Tetrahedron Letters, 1347 (1980). This isomerization is performed either on the isolated product IVb or on the product IVb mixed with pseudoionone IVa.

It is preferable to avoid the formation of the product of formula IVc; therefore, in order to increase the selectivity and to increase the reactivity, it is preferable to perform the process while employing a dinitrile as solvent. In these conditions, it is possible to carry out the process at a temperature preferably between about 0° C. and 30° C.

The process according to the invention is carried out with a mixture of compounds of formulas IIIa and IIIb, which compounds form an embodiment of the present invention. Compounds of formulas IIIa and IIIb may be obtained by sodium-catalyzed transesterification of the methyl β-ketoesters obtained by condensing myrcene with ethyl acetylacetate in the conditions described in European Patent EP 44,771.

Formula IIIa can also be obtained by condensing geranyl chloride with allyl acetoacetate which is anionized beforehand, for example by means of a sodium metal or an alkali metal hydride such as sodium hydride. The operation is carried out in an anhydrous organic solvent selected from ethers such as tetrahydrofuran. Allyl acetoacetate can be obtained according to the process described by W. Kimel et al., J. Amer. Chem. Soc., 65, 1992 (1943).

The following examples are intended to illustrate the invention without limitation.

EXAMPLE 1

2.78 g (10 mmol) of allyl 2-acetyl-5,9-dimethyl-4,8-decadienoate, 45 mg of palladium acetate and 10 cc of acetonitrile were introduced under argon atmosphere into a 50-cc three-necked round bottom flask. This was heated to reflux for 1 hour and 30 minutes. The reaction mixture was cooled and then extracted with pentane.

The solvent was evaporated and 1.78 g of a crude product was obtained, containing pseudoionone and geranylacetone in the molar ratio of 91/9 and a yield of 93%. The structure of the products obtained was confirmed by vapor phase chromatography analysis and by infrared, mass and proton nuclear magnetic resonance spectra.

The allyl 2-acetyl-5,9-dimethyl-4,8-decadienoate employed as starting material was prepared in the following manner:

15.4 g (0.1 mole) of allyl acetoacetate, 70 cc of tetrahydrofuran and 2.3 g of sodium metal were introduced under argon atmosphere into a 250-cc three-necked round bottom flask, and left in contact for 2 hours; then 17.5 g (0.1 mole) gernayl chloride was added. The mixture was heated to reflux for 16 hours. After cooling, the reaction mixture was poured into 400 cc saturated brine and was then extracted with pentane. After drying the organic phase over sodium sulphate, filtering and evaporating off the solvent, 26.1 g of a crude product was obtained which, by distillation at 128–131° C under reduced pressure (0.3 mm of mercury; 0.04 kPa) yielded 19.5g of allyl 2-acetyl-5,9-dimethyl-4,8-decadienoate whose purity was better than 90% with a yield of close to 70%. The structure of the product obtained was confirmed by the infrared, mass and proton nuclear magnetic resonance spectra.

EXAMPLE 2

2.78 g (10 mmol) of a 55/45 mixture of the allyl β-ketoesters denoted by formulas IIIa and IIIb, 24 mg of palladium acetate and 10 cc of adiponitrile were introduced under argon atmosphere into a 50-cc three-necked round bottom flask. The reaction mixture was stirred at 20° C. for 1 hour.

Vapor phase chromatography analysis of the crude reaction produce indicated a degree of conversion of 100% and a reaction yield of 91%. The product obtained consisted of:

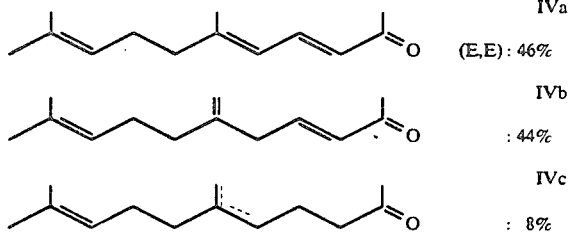

IVa (E,E): 46%

IVb : 44%

IVc : 8%

The structure of the products obtained was confirmed by the mass spectrum, the infrared spectrum and the proton nuclear magnetic resonance spectrum, which were examined in combination with vapor phase chromatography.

A 55/45 mixture of the allyl β-ketoesters of formulas IIIa and IIIb were obtained in the following manner:

84 g (1.45 moles) of allyl alcohol was introduced under argon atmosphere into a 250-cc three-necked round bottom flask, and 0.34 g of sodium metal was then added. When all the sodium had dissolved, 70 g (0.28 moles) of the mixture of methyl β-ketoesters was added and the reaction mixture was then heated to 90° C. for 6 hours and 15 minutes. Excess allyl alcohol was removed by distillation and 54g of the 55/45 mixture of the allyl β-ketoesters whose purity was close to 95%, was then isolated (b.p. (at 0.013 kPA)=121° C.). The structure of the product obtained was confirmed by the infrared spectrum, the mass spectrum and the proton nuclear magnetic resonance spectrum.

EXAMPLES 3 to 7

The procedure of Example 2 was repeated with the conditions given in Table I.

TABLE I

| | | | | Results | | | | |
|---|---|---|---|---|---|---|---|---|
| Example | Solvent | Catalyst | Conditions | DC % | Yld % | IVa % | IVb % | IVc % |
| 3 | Methylglutaronitrile | Pd(OAc)₂ 1% | 20° C. 2 hours | 95 | 92 | 42 | 45 | 13 |
| 4 | 1,6-Dicyanohexane | Pd(OAc)₂ 1% | 20° C. 2 hours | 98 | 90 | 43 | 48 | 9 |
| 5 | Acetonitrile | Pd(OAc)₂ 3.4% | 90° C. 1 hour | 100 | 88 | 46 | 32 | 22 |
| 6 | Benzonitrile | Pd(OAc)₂ 1% | 80° C. 1 hour | 100 | 89 | 48 | 40 | 12 |
| 7 | Benzonitrile | Pd(dba)₂ | 80° C. 1 hour | 100 | 93 | 52 | 39 | 9 |

We claim:

1. A process for the preparation of compounds of formula IVa or formula IVb or mixtures thereof:

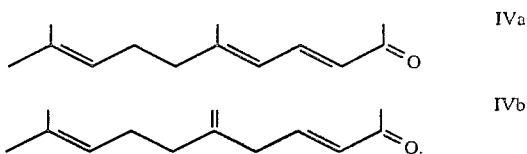

comprising oxidative decarboxylation of an α-monosubstituted allyl β-ketoester of formula IIIa or formula IIIb or mixtures thereof:

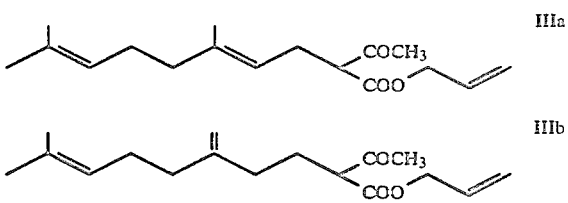

whereby said decarboxylation is carried out in an organic solvent selected from amides, nitriles and dinitriles in the presence of a palladium-based catalyst.

2. The process according to claim 1, wherein the organic solvent is selected from dimethylformamide, acetonitrile, benzonitrile, methylglutaronitrile, adiponitrile and 1,6-dicyanohexane.

3. The process according to claim 1, wherein the organic solvent is a dinitrile.

4. The process according to claim 1, wherein the palladium-based catalyst is selected from Pd(OAc)$_2$ and Pd(dba)$_2$.

5. The process according to claim 1, wherein the decarboxylation is carried out in the presence of a ligand.

6. The process according to claim 4, wherein the ligand is selected from triphenylphosphine and diphenylphosphinoethane.

7. The process according to claim 1, wherein the decarboxylation is carried out at a temperature of between about 0° C. and the reflux temperature of the reaction mixture.

8. The process according to claim 1, wherein the decarboxylation is carried out at a temperature of between about 0° C. and 30° C.

9. A compound of formula:

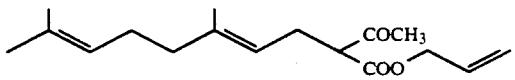

10. A compound of formula:

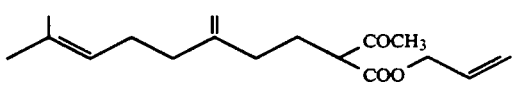

* * * * *

UNITED STATES PATENT AND TRADEMARK OFFICE
CERTIFICATE OF CORRECTION

PATENT NO. : 5,102,581
DATED : April 07, 1992
INVENTOR(S) : Claude Mercier et al.

It is certified that error appears in the above-identified patent and that said Letters Patent is hereby corrected as shown below:

Claim 6, column 5, line 9, change "claim 4" to --claim 5--.

Signed and Sealed this

Twenty-first Day of December, 1993

Attest:

BRUCE LEHMAN

Attesting Officer          Commissioner of Patents and Trademarks